United States Patent [19]
MacLean et al.

[11] Patent Number: 6,057,309
[45] Date of Patent: May 2, 2000

[54] COMBINATION THERAPY TO PREVENT BONE LOSS-PROGESTERONE AND ESTROGEN AGONISTS

[75] Inventors: David B. MacLean, Providence, R.I.; David D. Thompson, Gales Ferry, Conn.

[73] Assignee: Pfizer Inc., New York, N.Y.

[21] Appl. No.: 09/193,265

[22] Filed: Nov. 16, 1998

Related U.S. Application Data

[63] Continuation of application No. 08/803,710, Feb. 21, 1997, abandoned
[60] Provisional application No. 60/012,400, Feb. 28, 1996.

[51] Int. Cl.[7] ......................... A61K 31/56; A61K 31/135
[52] U.S. Cl. ........................................... 514/171; 514/648
[58] Field of Search ...................... 514/648, 171

[56] References Cited

U.S. PATENT DOCUMENTS

| | | | |
|---|---|---|---|
| 5,047,431 | 9/1991 | Schickaneder et al. | 514/648 |
| 5,254,594 | 10/1993 | Niikura et al. | 514/648 |
| 5,384,332 | 1/1995 | Fontana | 514/648 |
| 5,441,986 | 8/1995 | Thompson | 514/648 |
| 5,455,275 | 10/1995 | Fontana | 514/648 |
| 5,550,164 | 8/1996 | Fontana | 514/648 |

FOREIGN PATENT DOCUMENTS

| | | | |
|---|---|---|---|
| 0665015 | 2/1995 | European Pat. Off. | A61K 31/57 |
| WO9924027 | 5/1999 | WIPO | 514/171 |

OTHER PUBLICATIONS

Patent Abstract of Japan, vol. 095, No. 002, Mar. 31, 1995.
Hasmann, et al., Cancer Letters, vol. 84(2), pp. 101–116 (1994).

*Primary Examiner*—Jerome D. Goldberg
*Attorney, Agent, or Firm*—Peter C. Richardson; Paul H. Ginsburg; Jolene W. Appleman

[57] ABSTRACT

The present invention provides novel methods of inhibiting bone loss comprising administering to a mammal in need of such treatment an effective amount of a compound of formula I

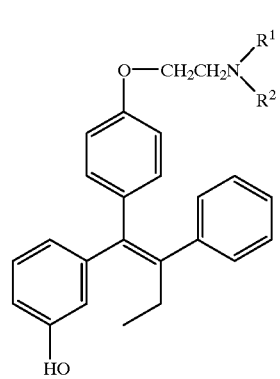

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof; together with a progestin.

4 Claims, No Drawings

COMBINATION THERAPY TO PREVENT BONE LOSS-PROGESTERONE AND ESTROGEN AGONISTS

This application is a continuation of U.S. patent application Ser. No. 08/803,710, filed Feb. 21, 1997, now abandoned, which was a continuation of U.S. Provisional Application Ser. No. 60/012400 filed Feb. 28, 1996.

This is a continuation of provisional application Ser. No. 60/012,400 filed Feb. 28, 1996, the benefit of which is hereby claimed under 37 C.F.R. §1.78(a)(3).

BACKGROUND OF THE INVENTION

Osteoporosis describes a group of diseases which arise from diverse etiologies, but which are characterized by the net loss of bone mass per unit volume. A consequence of this loss of bone mass is the failure of the skeletal frame to provide adequate structural support for the body, resulting in bone fracture. One of the most common types of osteoporosis occurs in women shortly after menopause. Most women lose between 20–60% of the bone mass in the trabecular compartment of the bone within 3–6 years after the cessation of menses. This rapid loss of bone mass is generally associated with an increase of both bone resorption and formation. The resorptive cycle is more dominant, however; and the result is a net loss of bone mass.

Thus, osteoporosis is a common and serious disease among post-menopausal women. An estimated 25 million women in the United States alone are afflicted with this disease. The results of this disease are both personally and economically harmful. Large economic losses are due to its chronic nature and the need for extensive and long term support (hospitalization and nursing home care) from the disease sequelae. The losses are especially great in more elderly patients. Additionally, although osteoporosis is not generally considered a life threatening condition, there is a 20–30% mortality rate related to hip fractures in elderly women. A large percentage of this mortality rate can be directly associated with post-menopausal osteoporosis.

The tissue in the bone most vulnerable to the effects of post-menopausal osteoporosis is the trabecular bone. This tissue is often referred to as spongy or cancellous bone and particularly concentrated near the ends of the bone, near the joints and in the vertebrae of the spine. Trabecular tissue is characterized by small osteoid structures which interconnect with each other and with the more solid and dense cortical tissue that makes up the outer surface and central shaft of the bone. This criss-cross network of trabeculae gives lateral support to the outer cortical structure and is critical to the bio-mechanical strength of the overall structure. It is primarily the net resorption and loss of the trabeculae which leads to the failure and fracture of bone in post-menopausal osteoporosis. In light of the loss of the trabeculae in post-menopausal women, it is not surprising that the most common fractures are those associated with bones which are highly dependent on trabecular support, e.g., the vertebrae, the neck of the weight bearing bones (femur) and the forearm. Indeed, hip fracture, collies fractures, and vertebral crush fractures are hall-marks of post-menopausal osteoporosis.

A very important concept in the treatment and study of post-menopausal osteoporosis is the concept of fracture threshold. The fracture threshold is the point at which the bone density (therefore, the bone strength) decreases to a value where there is a high probability of bone fracture. This point is not a particular value for all women but rather a relative number for an individual and is dependent on a number of factors such as weight, life-style, or other risks which might contribute to the possibility of bone fracture.

In general, most pre-menopausal women have bone densities above the fracture threshold, and there is a low probability that a fracture will occur. A woman's pre-menopausal bone density and the rate of bone loss after menopause will determine when, or if, she will cross the threshold and be at risk for fracture. For women who present with fractures due to osteoporosis, ideal therapy would be to increase bone density (strength) to a value above the fracture threshold. Alternatively, for women whose bone density is still above the threshold, it would be advantageous to keep them above it.

Today, the only available effective treatment for post-menopausal osteoporosis is hormone replacement therapy, specifically estrogen replacement because post-menopausal women are estrogen deficient. The mechanism of action of estrogen in the treatment of osteoporosis is not well understood; however, it is generally agreed that it inhibits bone resorption. The net effect of the estrogen replacement therapy (ERT) is to keep the woman's bone density at the level at which therapy was initiated, i.e., it maintains bone density. If a woman is above the fracture threshold when (ERT) is initiated, and if ERT is maintained, she will remain above the threshold and be at low risk for fracture. This fact would argue for the placement of women on ERT at or soon after the cessation of menses.

For women whose bone density has already fallen below the fracture threshold, however, ERT will only maintain bone density at the level at which they began therapy. Thus, these women will remain below the threshold and will be at further risk for fracture. ERT is still advisable for these women because it will keep a bad situation from getting worse. It would clearly be advantageous, however, to have a therapy which would boost bone density above the fracture threshold to more normal levels and then maintain it. Currently, there are no effective approved therapies which demonstrate an ability to increase bone density to such a level.

As noted, ERT is now the only effective approved treatment for post-menopausal osteoporosis. In those women who do not have a uterus, estrogen (usually given as a conjugated form of estrone) can be given by itself. In most post-menopausal women who have a uterus, however, unopposed estrogen increases the risk of endometrial cancer. Thus, a progestin is often also administered, either as a combination or in cyclical therapy, to reduce that risk.

"Antiestrogen" is a term that "has been rather broadly applied to several different types of compounds that inhibit or modify the action of estrogen. Progestins and androgens have been described as antestrongenic . . . " (Goodman and Gilman, *The Pharmacological Basis of Therapeutics*, 6th Ed., p 1431.) In addition, certain synthetic compounds, such as tamoxifene, clomiphene, droloxifene and nafoxidine, are called antiestrogens and have been shown both experimentally and clinically to block some of the effects of estrogen. The synthetic "antiestrogens" were principally developed for the treatment of estrogen-dependent breast carcinoma. These compounds are classical mixed agonist/antagonists which demonstrate some estrogenic activity. For example, tamoxiene, the most widely used antiestrogen, has been shown to have estrogenic effects in humans.

The combination of certain 3-benzoyl-benzothiophenes and a progestin has been found to be effective in preventing bone loss. EP 665,015 A2.

SUMMARY OF THE INVENTION

The present invention relates to methods for inhibiting bone loss comprising administering to a mammal in need of such treatment an effective amount of a compound of formula I

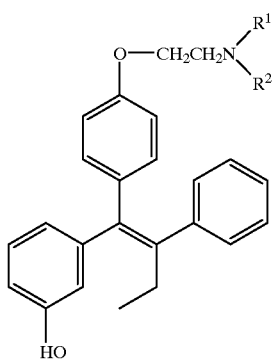

(I)

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof; together with an effective amount of a progestin. Preferred progestins are medroxyprogesterone, norethindrone or norethynodrel. A preferred compound of formula I is that in which $R^1$ and $R^2$ are methyl. A preferred salt is the citrate salt.

DETAILED DESCRIPTION OF THE INVENTION

The present invention concerns methods for inhibiting bone loss. The term "inhibit" is defined to include its generally accepted meaning which includes prophylactically treating a subject to prevent the occurrence of one or more of these conditions or disease states, holding in check the symptoms of such a condition or disease state, and/or treating such symptoms. Thus, the present methods include both medical therapeutic and/or prophylactic treatment, as appropriate.

The methods of this invention are practiced by administering to an individual in need of treatment an effective amount of a compound formula I

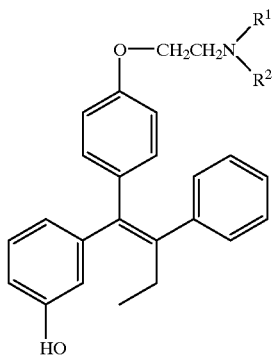

(I)

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof; together with an effective amount of a progestin selected from medroxyprogesterone, norethindrone and norethynodrel.

Progestins are available from commercial sources and include: Algestone Acetophenide, Altrenogest, Amadinone Acetate, Anagestone Acetate, Chlormadinone Acetate, Cingestol, Clogestone Acetate, Clomegestone Acetate, Delmadinone Acetate, Desogestrel, Dimethisterone, Dydrogesterone, Ethynerone, Ethynodiol Diacetate, Etonogestrel, Flurogestone Acetate, Gestaclone, Gestodene, Gestonorone Caproate, Gestrinone, Haloprogesterone, Hydroxyprogesterone Caproate, Levonorgestrel, Lynestrenol, Medrogestone, Medroxyprogesterone Acetate, Melengestrol Acetate, Methynodiol Diacetate, Norethindrone, Norethindrone Acetate, Norethynodrel, Norgestimate, Norgestomet, Norgestrel, Oxogestone Phenpropionate, Progesterone, Quingestanol Acetate, Quingestrone, and Tigestol.

Preferred progestins are medroxyprogestrone, norethindrone and norethynodrel.

Dosage of progestins is about 0.1 to 10 mg per day; the preferred dose is about 0.25 to 5 mg per day in combination with a compound of formula I.

Compounds of formula I are known in the art and essentially are prepared via the methods described in U.S. Pat. No. 5,047,431, which is hereby incorporated herein by reference.

A preferred formula I compound is that in which $R^1$ and $R^2$ each are methyl. This preferred compound is known as droloxifene, (E)-1-[4'-(2-Dimethylaminoethoxy)phenyl]-1-(3-hydroxyphenyl)-2-phenylbut-1-ene, which previously has been described as an antiestrogenic agent and is useful for the treatment of hormone dependent mammary tumors (U.S. Pat. No. 5,047,431), and for the relief of bone diseases caused by the deficiency of estrogen or the like (U.S. Pat. No. 5,254,594). Furthermore, droloxifene is known to have less uterotrophic effect than other antiestrogenic compounds such as tamoxifen.

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate,β-hydroxybutyrate, butyne-1,4dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the citrate salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts of formula I compounds generally have enhanced solubility characteristics compared to the compound from which they are derived, and thus are often more amenable to formulation as liquids or emulsions.

Once prepared, the free base or salt form of formula I compounds and a progestin can be administered to an individual in need of treatment for the methods herein described. The following nonlimiting test examples illustrate the methods of the present invention.

For the methods of the present invention, compounds of Formula I and a progestin are administered continuously, or from 1 to 4 times daily.

As used herein, the term "effective amount" means an amount of the composition used in the methods of the present invention which is capable of inhibiting the symptoms of the pathological conditions herein described. The specific dose of a compounds administered according to this invention will, of course, be determined by the particular circumstances surrounding the case including, for example, the compounds administered, the route of administration, the state of being of the patient, and the severity of the pathological condition being treated. A typical daily dose will contain a nontoxic dosage level of from about 0.25 mg to about 100 mg/day of a composition of the present invention. Preferred daily doses generally will be from about 1 mg to about 20 mg/day. The compound of formula I will be administered concurrently with about 0.1 mg to 10 mg of a progestin.

The compounds of this invention can be administered by a variety of routes including oral, rectal, transdermal, subucutaneous, intravenous, intramuscular, and intranasal. These compounds preferably are formulated prior to administration, the selection of which will be decided by the attending physician. Typically, a formula I compound, or a pharmaceutically acceptable salt thereof, is combined with a pharmaceutically acceptable carrier, diluent or excipient to form a pharmaceutical formulation.

The total active ingredients in such formulations comprises from 0.1% to 99.9% by weight of the formulation. By "pharmaceutically acceptable" it is meant the carrier, diluent, excipients, and/or salt must be compatible with the other ingredients of the formulation, and not deleterious to the recipient thereof.

Pharmaceutical formulations containing a compound of formula I can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate agents for retarding dissolution such as paraffin resorption accelerators such as quatemary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I and progestin generally will be administered in a convenient formulation. The following formulation examples only are illustrative and are not intended to limit the scope of the present invention.

In the formulations which follow, "active ingredient" means a compound of formula 1, or a salt thereof; and a progestin.

Formulation 1: Gelatin Capsules

Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredient are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of medicament per 5 ml dose are made as follows:

Formulation 4: Suspensions

| Ingredient | Quantity (mg/5 ml) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The medicament is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool. An intravenous formulation is prepared as follows:

Formulation 7: Intravenous Solution

| Ingredient | Quantity |
| --- | --- |
| Active ingredient | 20 mg |
| Isotonic saline | 1,000 mL |

The solution of the above ingredients is intravenously administered to a patient at a rate of about 1 mL per minute.

Example 1

In these examples, a model of post-menopausal osteoporosis is used in which effects of different treatments upon femur density are determined.

Seventy-five day old female Sprague Dawley rats (weight range of 225 to 275 g) are obtained from Charles River Laboratories (Portage, Mich.). They are housed in groups of 3 and have ad libitum access to food (calcium content approximately. 1%) and water. Room temperature is maintained at 22.2°±1.7° C. with a minimum relative humidity of 40%. The photoperiod in the room is 12 hours light and 12 hours dark.

One week after arrival, the rats undergo bilateral ovariectomy under anesthesia (44 mg/kg Ketamine and 5 mg/kg Xylazine (Butler, Indianapolis, Ind.) administered intramuscularly). Treatment with vehicle or a compound of formula I and a progestin is initiated either on the day of surgery following recovery from anesthesia or 35 days following the surgery.

Oral dosage is by gavage in 0.5 mL of 1% carboxymethylcellulose (CMC).

Body weight is determined at the time of surgery and weekly during the study, and the dosage is adjusted with changes in body weight. Vehicle-treated ovariectomized (ovex) rats and non-ovariectomized (intact) rats are evaluated in parallel with each experimental group to serve as negative and positive controls.

The rats are treated daily for 35 days (6 rats per treatment group) and sacrificed by decapitation on the 36th day. The 35-day time period is sufficient to allow maximal reduction in bone density, measured as described infra. At the time of sacrifice, the uteri are removed, dissected free of extraneous tissue, and the fluid contents were expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and scanned at the distal metaphysis 1 mm from the patellar groove with single photon absorptiometry. Results of the densitometer measurements represent a calculation of bone density as a function of the bone mineral content and bone width.

What is claimed is:

1. A method for inhibiting bone loss comprising administering to a mammal in need of such treatment an effective enhanced amount of a compound of formula I

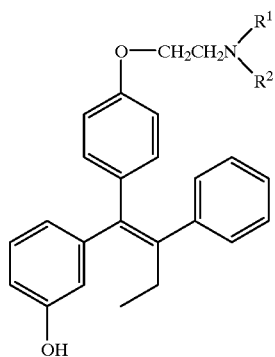

(I)

wherein $R^1$ and $R^2$ may be the same or different provided that when $R^1$ and $R^2$ are the same, each is a methyl or ethyl group, and when $R^1$ and $R^2$ are different, one of them is a methyl or ethyl group and the other is hydrogen or a benzyl group; or a pharmaceutically acceptable salt thereof; together with an effective enhanced amount of a progestin.

2. A method according to claim 1 wherein the compound of formula I is a compound wherein $R^1$ and $R^2$ each are methyl, or a pharmaceutically acceptable salt thereof.

3. A method according to claim 2 wherein said salt thereof is the citrate salt.

4. A method according to claim 1 wherein said progestin is selected from the group consisting of medroxyprogesterone, norethindrone and norethynodrel.

* * * * *